United States Patent [19]

Holmes et al.

[11] B 4,006,161
[45] Feb. 1, 1977

[54] THIO-SUBSTITUTED 2-OXO-INDOLINES

[75] Inventors: Richard E. Holmes, Indianapolis; Glen P. Jourdan, Martinsville, both of Ind.

[73] Assignee: Eli Lilly and Company, Indianapolis, Ind.

[22] Filed: Dec. 26, 1973

[21] Appl. No.: 427,946

[44] Published under the second Trial Voluntary Protest Program on March 23, 1976 as document No. B 427,946.

[52] U.S. Cl. .............................. 260/325 R; 424/274
[51] Int. Cl.$^2$ ...................................... C07D 209/34
[58] Field of Search ................................ 260/325 R

[56] References Cited

UNITED STATES PATENTS 3,767,653  10/1973  Krapcho ..................... 260/325 R

OTHER PUBLICATIONS

Gassman et al., "Chem. Abstracts," vol. 78, p. 394, No. 159359f, (1973).

*Primary Examiner*—Lewis Gotts
*Assistant Examiner*—S. P. Williams
*Attorney, Agent, or Firm*—William C. Martens, Jr.; Everet F. Smith

[57] ABSTRACT

Thio-substituted 2-oxoindolines have the formula

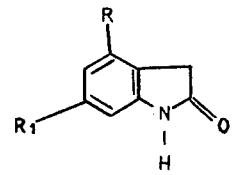

in which one of R or $R_1$ is hydrogen and the other is $R_2$—S—, in which $R_2$ is $C_1$–$C_3$ alkyl, benzyl, halobenzyl, nitrobenzyl, $C_1$–$C_3$ alkylbenzyl, or phenyl. These compounds are active in relieving a condition associated with anxiety, tension, or like emotional disturbances.

5 Claims, No Drawings

THIO-SUBSTITUTED 2-OXO-INDOLINES

BACKGROUND AND SUMMARY OF THE INVENTION

This invention relates to compounds having therapeutic activity, to therapeutic compositions, and to a process for achieving therapeutic action.

It has been discovered that certain substituted 2-oxo-indolines have a useful effect on the central nervous system. In particular, it has been discovered that these compounds exhibit a sedative-hypnotic effect and can be used in the treatment of conditions associated with anxiety, tension, or other emotional disturbances.

2-Oxo-indolines are widely recognized in the art; see, for example, British Pat. No. 1,247,113; and Belgian Pat. No. 756,447. Nowhere, however, does the art recognize 2-oxo-indolines having the specific structure of the compounds of this invention; furthermore, nowhere does the art recognize the useful therapeutic activity of 2-oxo-indolines which forms the basis of this invention.

Specifically, this invention relates to a compound of the formula

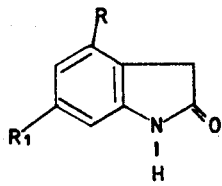

in which one of R or $R_1$ is hydrogen and the other is $R_2$—S—, in which $R_2$ is $C_1$–$C_3$ alkyl, benzyl, halobenzyl, nitrobenzyl, $C_1$–$C_3$ alkylbenzyl, or phenyl.

This invention is also directed to a pharmaceutical composition for relieving a condition associated with anxiety, tension, or like emotional disturbances comprising a therapeutically effective dose of an oxo-indoline of the foregoing formula in association with a pharmaceutical carrier.

Another embodiment of this invention relates to a method of treating a patient to relieve a condition associated with anxiety, tension, or like emotional disturbance which comprises administering to said patient a compound of the foregoing formula.

DETAILED DESCRIPTION OF THE INVENTION

The compounds of this invention have the formula

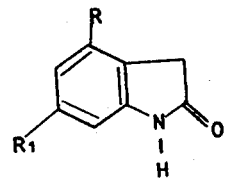

Illustrative of these are the following:
2-Oxo-4-methylthioindoline;
2-Oxo-6-methylthioindoline;
2-Oxo-4-ethylthioindoline;
2-Oxo-6-ethylthioindoline;
2-Oxo-4-(1-propylthio)indoline;
2-Oxo-6-(1-propylthio)indoline;
2-Oxo-4-(2-propylthio)indoline;
2-Oxo-6-(2-propylthio)indoline;
2-Oxo-4-benzylthioindoline;
2-Oxo-6-benzylthioindoline;
2-Oxo-4-(4-chlorobenzylthio)indoline;
2-Oxo-6-(3-bromobenzylthio)indoline;
2-Oxo-4-(4-nitrobenzylthio)indoline;
2-Oxo-6-(4-nitrobenzylthio)indoline;
2-Oxo-4-(3-methylbenzylthio)indoline;
2-Oxo-6-(4-isopropylbenzylthio)indoline;
2-Oxo-4-phenylthioindoline;
2-Oxo-6-phenylthioindoline; and the like.

Oxo-indolines such as the above can be prepared by the following specific sequence:

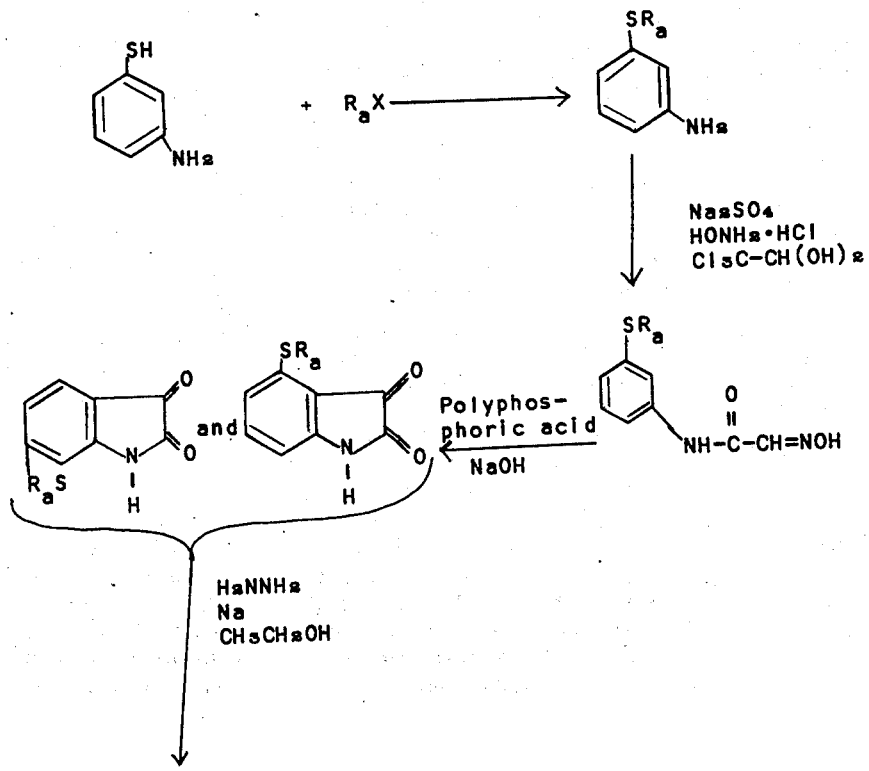

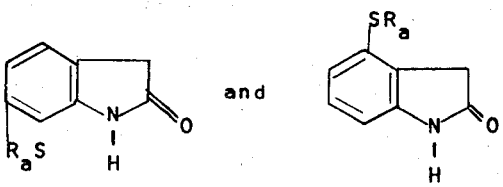 and

Thus, the source of the compounds of this invention can be *m*-aminothiophenol. Typically, *m*-aminothiophenol is reacted in an alkaline medium, for example, in the presence of an alkali metal hydroxide, with a halide having the formula $R_aX$ in which $R_a$ is the desired thio substituent in the final product and X is a halogen, for example, chlorine, bromine, or iodine. The mixture is permitted to react in a suitable inert medium, such as, for example, dioxane. Typically, the reaction is carried out at about room temperature for a period of from about 2 to about 20 hours. The product, an aniline having a substituted thio group in the meta position, is recovered by well known extraction techniques.

The resulting substituted aniline, in the form of its acid addition salt, is converted to the corresponding isonitrosoacetanilide by reaction with chloral hydrate in the presence of sodium sulfate followed by treatment of the resulting reaction mixture with hydroxylamine hydrochloride. The reaction typically is carried out in water with the reaction mixture being gently heated for a short period of time.

The next step in the synthesis of the compounds of this invention involves the conversion of the isonitrosoacetanilide to its corresponding isatin. This ring-closure reaction can be accomplished by treating the isonitrosoacetanilide with polyphosporic acid at a moderately elevated temperature. Since ring-closure occurs in the position ortho to the anilide nitrogen, two structures are formed, namely the 4-substituted isatin and the 6-substituted isatin. Separation of these products can be accomplished by a successive precipitation technique. The reaction product mixture is first brought into aqueous solution by addition of alkali. Precipitation of the two products is pH dependent, and the 4-substituted isatin is precipitated from the solution by acidifying the mixture to a pH of from about 3 to about 5. The 4-substituted isatin is then collected by filtration, and the filtrate is further acidified to about pH 1, the approximate pH at which the 6-substituted isatin product precipitates. This product is then separately collected. Both products can be purified by recrystallization from an appropriate solvent.

The final step in the synthesis of the compounds of this invention involves the separate conversions of the 4-substituted isatin and the 6-substituted isatin to their corresponding 2-oxo-4-substituted indoline and 2-oxo-6-substituted indoline, respectively. This can be accomplished in both instances by treating the isatin with anhydrous hydrazine at reflux in an appropriate moderately low boiling solvent such as a lower alkyl alcohol. The resulting treated isatin is then reacted reductively with a sodium alkoxide effectively to replace the keto function in the 3-position with a methylene group, thereby achieving formation of the indoline. Recovery can be accomplished by evaporating the solvent, dissolving the residue in water to achieve solution of the water-soluble by-products, and acidification of the mixture to produce precipitation of the final product. The final product can then be purified by recrystallization from a suitable solvent.

In accordance with this invention, the pharmaceutically active indolines can be administered alone or in association with a pharmaceutical carrier. The pharmaceutical carrier is selected on the basis of the chosen route of administration and in accordance with standard pharmaceutical practice. For example, the indolines can be administered orally, for example, alone in the form of capsules or in the form of tablets or capsules containing excipients such as starch, milk sugar, certain types of clay, and the like. The indolines can also be administered orally in the form of elixirs or oral suspensions which can contain coloring and/or flavoring agents. The indolines can also be administered parenterally, and, in this administration, they can be prepared in the form of sterile solutions containing other solutes such as saline or glucose in sufficient quantity to make the solution isotonic. In intramuscular administration, the indoline compositions can be prepared in an oil base such as a peanut or sesame oil.

The indolines of this invention are administered in pharmaceutically effective amounts. Generally, these will range from about 0.5 to about 500 milligrams per day, and preferably from about 2 to about 200 milligrams per day. However, in general, the dosage will depend upon particular circumstances which may differ from case to case. For example, the dosage levels will vary with the age, weight, and general health of the recipient as well as various other factors which may be peculiar to the particular recipient. In general, if the indoline is administered by a parenteral route, a lower dosage, for example, for about 0.1 milligram to about 250 milligrams of the indoline can be employed. Preferably the indoline composition is in unit dosage form. This expression as used herein refers to a physically discrete unit containing a predetermined dose of the indoline either alone or in association with a pharmaceutically acceptable carrier or excipient. The unit dosage form may contain from about 0.5 to about 500 milligrams of the active indoline ingredient.

The following examples are provided to further illustrate the teaching of this invention and are by no means intended to be limiting upon the scope thereof.

EXAMPLE I

A. *m*-Isopropylthioaniline

To a stirring suspension of 25 grams (0.2 mole) of 3-aminothiophenol in 200 ml. of 5N NaOH was added drop-wise of solution of 24.6 grams of 2-bromopropane (0.20 mole; M.W. 123.00) dissolved in 100 ml. of 1,4-dioxane. The resulting suspension was stirred at room temperature overnight and then was extracted with two 500 ml. portions of ethyl ether. The ether extracts were combined, dried over $Na_2SO_4$, and evaporated in vacuo to yield 23.5 grams of m-isopropylthioaniline.

B. m-Isopropylthioisonitrosoacetanilide

To a solution of 111.0 grams of powdered sodium sulfate and 25.8 grams of chloral hydrate in 400 ml. of water was added a solution of 23.5 grams of m-isopropylthioaniline (0.141 mole; M.W. 167.25) and 12.5 ml. of conc. HCl in 300 ml. of water. A solution of 31.0 grams of hyydroxylamine hydrochloride dissolved in 75 ml. of water was then added. The resulting suspension was heated just to its boiling point and then was cooled in an ice water bath. One liter of ethyl ether was then added to the reaction mixture, and the resulting suspension was stirred for one hour. The ether layer was then separated from the aqueous layer, dried over $Na_2SO_4$, and evaporated in vacuo to yield 35 grams of m-isopropylthioisonitrosoacetanilide. Attempts to crystallize the product failed.

C. 6-Isopropylthioisatin

A 5 gram portion of m-isopropylthioisonitrosoacetanilide was heated with 25 grams of polyphosphoric acid in an 85°C. oil bath while stirring continuously with a thermometer. At about 80°C. the reaction became quite vigorous, and the mixture was placed immediately in an ice water bath, and, after cooling, the reaction mixture was diluted with 200 ml. of water. The resulting gummy solids were isolated by decanting the aqueous portion of the mixture. The solids were then slurried with 35 ml. of 5N NaOH for 30 minutes; the resulting alkaline solution was filtered through Celite and acidified with HCl to pH 3.0. A minor amount of a gummy precipitate formed and was collected. Further acidification to pH 1.0 produced a second precipitate which was collected and crystallized from chloroform/hexane to give 6-isopropylthioisatin, m.p. of 169°–180°C.

Analysis, Calculated for $C_{11}H_{11}NO_2S$: C, 59.71; H, 5.01; N, 6.33. Found: C, 59.48; H, 4.81; N, 6.22.

D. 2Oxo-6-(2-propylthio)indoline

A solution of 1.0 gram of 6-isopropylthioisatin (0.0045 mole; M.W. 221.27) and 4 ml. of 97 percent anhydrous hydrazine in 35 ml. of ethanol was refluxed for 2½ hours. The hot reaction solution was added to a solution of 0.5 gram of sodium in 30 ml. of ethanol. The resulting solution was refluxed for 3 hours and then allowed to cool. The reaction mixture was evaporated in vacuo to dryness, and the residue was diluted with 150 ml. of ice water and then acidified to pH 1.0 with conc. HCl. The resultant suspension was extracted twice with 150 ml. of ethyl acetate. The extracts were combined, dried over $Na_2SO_4$, and evaporated in vacuo. Attempts to crystallize the residue failed, and it was chromatographed over 100 grams silica gel using 1:1 ethyl acetate/hexane. Evaporation of the pure fractions yielded a crystalline produce which was recrystallized from cyclohexane to give 2-oxo-6-(2-propylthio)indoline, m.p. of 99°–102°C.

Analysis, Calculated for $C_{11}H_{13}NOS$: C, 63.74; H, 6.32; N, 6.76; S, 15.47. Found: C, 63.51; H, 6.17; N, 6.68; S, 15.22.

EXAMPLE II

A. m-Benzylthioaniline

To a stirring suspension of 25 grams (0.20 mole; M.W. 125.19) of 3-aminothiophenol in 200 ml. of 5N NaOH was added dropwise a solution of 34.2 grams of α-bromotoluene (0.20 mole; M.W. 171.04) dissolved in 100 ml. of 1,4-dioxane. The addition required about 30 minutes. The reaction mixture was stirred at room temperature for 2 hours and then extracted with two 500 ml. portions of ethyl ether. The extracts were combined, dried over $Na_2SO_4$, and evaporated to yield 41.0 grams of m-benzylthioaniline.

B. m-Benzylthioisonitrosoacetanilide

To a solution of 148.5 grams of powdered sodium sulfate and 35.0 grams of chloral hydrate in 550 ml. of water was added a solution of 41.0 grams of m-benzylthioaniline (0.191 mole; M.W. 215.19) and 16.85 ml. of conc. HCl in 300 ml. of water, followed by a solution of 42.0 grams of hydroxylamine hydrochloride in 100 ml. of water. The resulting suspension was heated just to boiling and then was cooled with an ice water bath. One liter of ethyl ether was then added to the mixture, and the resulting suspension was stirred for 1½ hours. The ether layer was separated from the aqueous layer, dried over sodium sulfate, and evaporated in vacuo to yield 51.05 grams of residue. Crystallization from chloroform gave m-benzylthioisonitrosoacetanilide, m.p. 260°–262°C.

Analysis, Caalculated for $C_{15}H_{14}N_2O_2S$: C, 62.92; H, 4.93; N, 9.78; S, 11.20. Found: C, 62.76; H, 4.66; N, 9.53; S, 11.06.

C. 2-Oxo-6-benzylthioindoline

A mixture of 9.0 grams of m-benzylthioisonitrosoacetanilide in 50 grams of polyphosphoric acid was heated in an 85°C. oil bath while stirring continuously with a thermometer. At about 80°C., a vigorous reaction occurred, and the mixture was immediately placed in an ice water bath. The reaction mixture was then diluted with 300 ml. of water. The mixture was stirred for 30 minutes, and the solids which formed were collected and suspended in 300 ml. of water. The solids were brought into solution by the addition of 1N NaOH. The solution was filtered, and the filtrate was acidified to pH 1.0 with conc. HCl. The resulting orange precipitate was collected and dried. The solid was combined with 2 ml. of 97 percent anhydrous hydrazine in 25 ml. of ethanol, and the mixture was refluxed for 6 hours. The hot solution was then added to a solution of 0.25 grams of sodium in 25 ml. of ethanol, and the resulting mixture was refluxed for 18 hours. After cooling, the reaction mixture was evaporated to dryness in vacuo, and 35 ml. of ice water were added to the residue. The mixture was acidified to pH 1.5 with conc. HCl. The aqueous suspension was then extracted twice with 50 ml. of ethyl acetate. The extracts were combined, dried over $Na_2SO_4$, and evaporated in vacuo after treatment with decolorizing carbon. The residue was crystallized twice from ethyl acetate to give 75 mg. of 2-oxo-6-benzylthioindoline, m.p. 132°–134°C.

Analysis, Calculated for $C_{15}H_{13}NOS$: C, 70.56; H, 5.13; N, 5.49; S, 12.56. Found: C, 70.53; H, 5.15; N, 5.70; S, 12.37.

EXAMPLE III

A. m-Ethylthioaniline

To a suspension of 25 grams (0.193 mole; M.W. 125.19) of 3-aminothiophenol in 200 ml. of 5N sodium hydroxide was added, dropwise, over a period of 1 hour, a solution of 29.9 grams (0.193 mole) of ethyl iodide in 50 ml. of 1,4-dioxane. The resulting suspension was allowed to stir at room temperature for 1 hour, 200 ml. of ethyl ether were then added, and stirring was continued for an additional 30 minutes. The ether layer was separated, washed with a saturated aqueous solution of sodium bisulfite, dried over $Na_2SO_4$, and evaporated in vacuo to yield 28.10 grams of m-ethylthioaniline.

B. m-Ethylthioisonitrosacetanilide

To a solution of 142.2 grams of powdered sodium sulfate and 33.5 grams of chloral hydrate in 550 ml. of water was added a solution of 28.10 grams (0.183 mole; M.W. 153.22) of m-ethylthioaniline and 16.15 ml. of conc. HCl in 150 ml. of water. A solution of 40.25 grams of hydroxylamine hydrochloride in 70 ml. of water was then added. The resulting suspension was heated to boiling and then cooled immediately in an ice water bath. After the reaction mixture had cooled, 700 ml. of ethyl ether were added, and the resulting suspension was stirred vigorously for 30 minutes. The ether layer was separated, dried over $Na_2SO_4$, and evaporated in vacuo. The residue was crystallized from chloroform to yield 18.55 grams of m-ethylthioisonitrosoacetanilide.

C. 4-Ethylthioisatin and 6-Ethylthioisatin

A suspension of 5.0 grams of m-ethylthioisonitrosoacetanilide in 25 grams of polyphosphoric acid was heated in an 85°C. oil bath with continuous stirring. At about 80°C. a vigorous reaction occurred, and the temperature increased rapidly to about 130°C. The reaction mixture was immediately placed in an ice water bath, and, after cooling, the mixture was diluted with 200 ml. ice water and stirred for 30 minutes. The solids were collected and washed with fresh water. The solids which formed then were suspended in 300 ml. of water and brought into solution by addition of 5N NaOH. the solution was filtered through Celite, and the filtrate was acidified with conc. HCl until precipitation occurred at pH 3.5. After stirring for 10 minutes, the precipitated solids were collected. Further acidification of the filtrate to pH 1.0 with concentrated HCl yielded a second precipitate.

The first precipitate was recrystallized from chloroform to give 4-ethylthioisatin, m.p. 171°–172°C. The second precipitate was also recrystallized from chloroform to give 6-ethylthioisatin, m.p. 213°–214°C.

Analysis, First Precipitate, Calculated for $C_{10}H_9NO_2S$: C, 57.95; H, 4.38; N, 6.76. Found: C, 57.81; H, 4.37; N, 6.78.

Analysis, Second Precipitate, Calculated for $C_{10}H_9NO_2S$: C, 57.95; H, 4.38; N, 6.76. Found: C, 57.68; H, 4.19; N, 6.63.

D. 2-Oxo-4-ethylthioindoline

A solution of 2.19 grams of 4-ethylthioisatin in 25 ml. of ethanol was refluxed with 4.4 ml. of 97 percent anhydrous hydrazine for 3 hours. The hot reaction solution was then added through a dropping funnel to a solution of 0.90 grams of sodium in 50 ml. of ethanol. The resulting solution was refluxed for 3½ hours and then allowed to cool. The reaction mixture was then evaporated to dryness in vacuo. The residue was diluted with 250 ml. of ice water and then acidified to pH 1.0 with conc. HCl. The resulting suspension was extracted twice with ethyl acetate. The extracts were combined, dried over sodium sulfate, and evaporated in vacuo. The residue was crystallized from ethyl acetate to yield 943 mg. of 2-oxo-4-ethylthioindoline, m.p. 143°–144°C.

Analysis, Calculated for $C_{10}H_{11}NOS$: C, 62.15; H, 5.74; N, 7.25; S, 16.59. Found: C, 61.98; H, 5.68; N, 7.25; S, 16.65.

E. 2-Oxo-6-ethylthioindoline

A solution of 4.01 grams (0.019 mole; M.W. 207.251) of 6-ethylthioisatin and 8 ml. of 97 percent anhydrous hydrazine in 100 ml. of ethanol was refluxed for 3½ hours. The hot reaction solution was then added through a dropping funnel to a solution of 1.61 grams of sodium in 100 ml. of ethanol. The resulting solution was refluxed for 3½ hours and then allowed to cool. The reaction mixture was evaporated in vacuo to an oily residue which was diluted with 250 ml. of ice water. The resulting suspension was then acidified to pH 1.0 with conc. HCl and extracted twice with ethyl acetate. The extracts were combined, washed with fresh water, dried over sodium sulfate, and evaporated in vacuo. The residue was crystallized from ethyl acetate to yield 1.53 grams of 2-oxo-6-ethylthioindoline, m.p. 125°–126.5°C.

Analysis, Calculated for $C_{10}H_{11}NOS$: C, 62.15; H, 5.74; N, 7.25; S, 16.59. Found: C, 61.93; H, 5.60; N, 7.03; S, 16.87.

EXAMPLE IV

A. m-Methylthioisonitrosoacetanilide

A solution of 93.5 grams of m-methylthioaniline (prepared by a procedure analogous to those of the previous examples), 59 ml. of conc. hydrochloric acid and 400 ml. of water was added dropwise to a solution of 122.5 grams of chloral hydrate and 777.5 grams of powdered sodium sulfate in 2 liters of water. A solution of 147.5 grams of hydroxylamine hydrochloride in 250 ml. of water was then added to the mixture. The resulting suspension was heated to boiling and then cooled immediately in an ice water bath. After the reaction mixture had cooled, 1 liter of ethyl ether was added, and the resulting mixture was stirred vigorously for about 45 minutes and then allowed to separate. The aqueous layer was separated from the ether layer, extracted with fresh ether, and discarded. The ether layer and the extract were combined, dried over $Na_2SO_4$, and evaporated in vacuo. Crystallization of the residue from chloroform gave m-methylthioisonitrosoacetanilide, m.p. 150°C.

Analysis, Calculated for $C_9H_{10}N_2O_2S$: C, 51.41; H, 4.79; N, 13.32; O, 15.22. S, 15.25. Found: C, 51.29; H, 4.81; N, 13.26; O, 15.41; S, 15.10.

B. 4-Methylthioisatin and 6-Methylthioisatin

A suspension of 3.0 grams of m-methylthioisonitrosoacetanilide in 20.0 grams of polyphosphoric acid was heated in an 85°C. oil bath while stirring continuously with a thermometer. At about 80°C. the reaction became quite vigorous, and the temperature increased rapidly to about 130°C. The mixture was immediately placed in an ice water bath, and, after cooling, was diluted with 75 ml. of water and stirred for 10 minutes. The solids were collected and washed with fresh water. The solids then were suspended in 100 ml. of water and brought into solution by the addition of 5N NaOH. The solution was filtered through Celite, and the filtrate was acidified with glacial acetic acid until precipitation occurred at pH 4.5. After stirring for five minutes the solids were collected. Further acidification of the filtrate to pH 1.0 with concentrated HCl yielded a second precipitate.

The first precipitate was crystallized from chloroform to give 4-methylthioisatin, m.p. 265°C. The second precipitate was crystallized from ethanol to give 6-methylthioisatin, m.p. 246°C.

Analysis, First Precipitate, Calculated for $C_9H_7NO_2S$: C, 55.94; H, 3.65; N, 7.25; S, 16.59. Found: C, 56.14; H, 3.46; N, 7.54; S, 16.29.

Analysis, Second Precipitate, Calculated for $C_9H_7NO_2S$: C, 55.94; H, 3.65; N, 7.25; S, 16.59. Found: C, 56.20; H, 3.47; N, 7.45; S, 16.88.

C. 2-Oxo-4-methylthioindoline

A solution of 6.15 grams (0.034 mole) of 4-methylthioisatin and 13 ml. of 97 percent hydrazine in 100 ml. of ethanol was heated at reflux for 3½ hours. The hot solution was then added through a dropping funnel to a solution of 2.90 grams of sodium in 100 ml. of ethanol heated to 65°C. The resulting solution was heated at reflux for 2½ hours and then allowed to cool to room temperature. The reaction mixture was evaporated to dryness in vacuo, and the residue was diluted with 300 ml. of ice water and acidified to pH 1.5 with conc. HCl. The resulting suspension was extracted with three 150 ml. portions of ethyl acetate. The extracts were combined, dried over $Na_2SO_4$, and evaporated in vacuo. The residue was crystallized from ethyl acetate to yield 3.37 grams of 2-oxo-4-methylthioindoline, m.p. 198°C.

Analysis, Calculated for $C_9H_9NOS$: C, 60.31; H, 5.06; N, 7.81; S, 17.89. Found: C, 60.18; H, 5.30; N, 8.01; S, 17.71.

D. 2-Oxo-6-methylthioindoline

A solution of 11.55 grams (0.0645 mole) of 6-methylthioisatin and 26 ml. of 97 percent hydrazine in 150 ml. of ethanol was heated at reflux for 3½ hours. The hot solution was then added through a dropping funnel to a solution of 5.35 grams of sodium in 150 ml. of ethanol heated to 65°C. The resulting solution was heated at reflux for 2½ hours and then allowed to cool to room temperature. The reaction mixture was evaporated to dryness in vacuo, and the residue was diluted with 300 ml. of ice water and acidified to pH 1.5 with conc. HCl. The resulting suspension was extracted with three 250 ml. portions of ethyl acetate. The extracts were combined, dried over $Na_2SO_4$, and evaporated in vacuo. The residue was crystallized from ethyl acetate to yield 7.38 grams of 2-oxo-6-methylthioindoline, m.p. 179°–180°C.

Analysis, Calculated for $C_9H_9NOS$: C, 60.31; H, 5.06; N, 7.81; S, 17.89. Found: C, 60.02; H, 5.32; N, 8.02; S, 17.57.

The activity of the indolines as tranquilizers can be demonstrated by their hypnotic effect on canaries. In this activity evaluation the test compound is placed into a 5 percent aqueous acacia suspension in an amount sufficient to provide a mixture containing 8 milligrams of test compound per milliliter. The individual weights of three canaries are determined, and a predetermined amount of the acacia suspension, measured in milligrams of test compound per kilogram of body weight of the canary, is orally injected. The birds are placed in a lighted area and observed for a period of one hour, and the length of time that each bird sleeps is noted.

In the Table following is provided the tranquilizing activity of the indolines of this invention as determined from the aforedescribed test procedure.

TABLE
ACTIVITY OF 2-OXO-INDOLINES

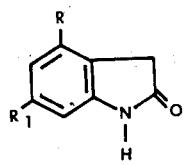

| | | Milligrams per kilogram weight of canary[a] | | | | | | | |
|---|---|---|---|---|---|---|---|---|---|
| | | 160 | | 80 | | 40 | | 20 | |
| R | $R_1$ | No. Slept | Min., Ave. | No. Slept | Min., Ave. | No. Slept | Min., Ave. | No. Slept | Min., Ave. |
| $CH_3S-$ | H | 1 | 8 | 1 | 7 | 0 | — | — | — |
| H | $CH_3S-$ | 3 | 37 | 2 | 32 | 3 | 18 | 0[b] | — |
| H | ⌬-$CH_2S$ | 1 | 17 | 1 | 7 | 0 | — | — | — |
| H | $CH_3CH_2S-$ | — | — | 1 | 3 | — | — | — | — |
| H | $(CH_3)_2CHS-$ | — | — | 1 | 2 | — | — | — | — |

[a] "No. Slept" refers to the number of canaries in the group of three canaries in which sleep was induced. "Min., Ave." refers to the combined total minutes of sleep which were recorded divided by three.
[b] One of the canaries became drowsy.

I claim:
1. A compound of the formula

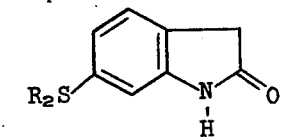

in which $R_2$ is $C_1$–$C_3$ alkyl, benzyl, halobenzyl, nitrobenzyl, $C_1$–$C_3$ alkylbenzyl, or phenyl.

2. Compound of claim 1, in which $R_2$ is $C_1$–$C_3$ alkyl.

3. Compound of claim 2, in which $R_2$ is methyl.

4. Compound of claim 1, in which $R_2$ is benzyl, halobenzyl, nitrobenzyl, or $C_1$–$C_3$ alkylbenzyl.

5. Compound of claim 4, in which $R_2$ is benzyl.

* * * * *